United States Patent
Mitchell

(10) Patent No.: US 7,850,631 B2
(45) Date of Patent: Dec. 14, 2010

(54) FOOT ABDUCTION BRACING APPARATUS

(76) Inventor: John R. Mitchell, 202 N. Madison St., Wayland, IA (US) 52654

( * ) Notice: Subject to any disclaimer, the term of this patent is extended or adjusted under 35 U.S.C. 154(b) by 0 days.

(21) Appl. No.: 12/211,658

(22) Filed: Sep. 16, 2008

(65) Prior Publication Data

US 2010/0069808 A1    Mar. 18, 2010

(51) Int. Cl.
*A61F 5/00* (2006.01)
(52) U.S. Cl. ............................................ 602/24
(58) Field of Classification Search ............... 602/24, 602/27–29; 36/140–144, 147, 154, 155, 36/160
See application file for complete search history.

(56) References Cited

U.S. PATENT DOCUMENTS

| | | | | |
|---|---|---|---|---|
| 4,412,536 A | * | 11/1983 | Kurtz et al. | 602/24 |
| 5,797,200 A | * | 8/1998 | Hess et al. | 36/97 |
| 7,267,657 B1 | | 9/2007 | Mitchell | |
| 2007/0073206 A1 | | 3/2007 | Hatton et al. | |

FOREIGN PATENT DOCUMENTS

DE    20212504 U1    12/2002

OTHER PUBLICATIONS

European Search Report dated Jan. 13, 2010 from counterpart European application.

* cited by examiner

*Primary Examiner*—Patricia M Bianco
*Assistant Examiner*—Camtu T Nguyen
(74) *Attorney, Agent, or Firm*—Brett D. Papendick; Shuttleworth & Ingersoll, PLC

(57) ABSTRACT

An improved foot abduction brace device in which the shoe are connected by an abduction bar which is a single bar that can be bent by the treating heal care professional to hold the shoes in the desired angles of abduction and dorsiflexion. The abduction bar is bent near the heel portion of the shoe and is made of a material that allows the bar to retain the selected position once bent. However, the bar is sufficiently strong so that the child cannot bend the bar and therefore change the selected angles.

10 Claims, 3 Drawing Sheets

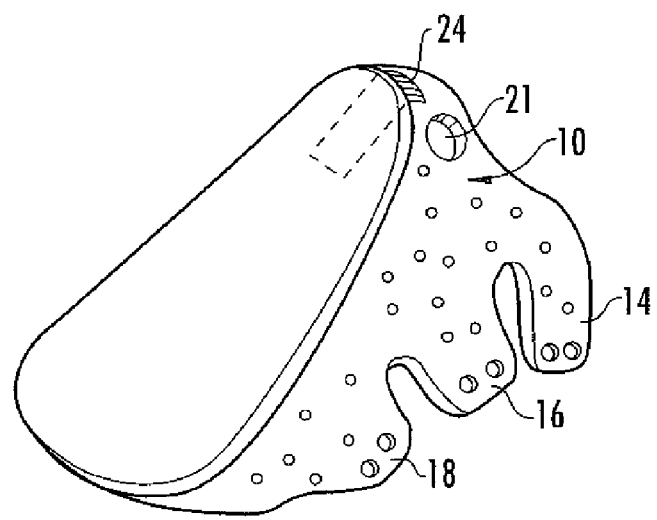
FIG. 4
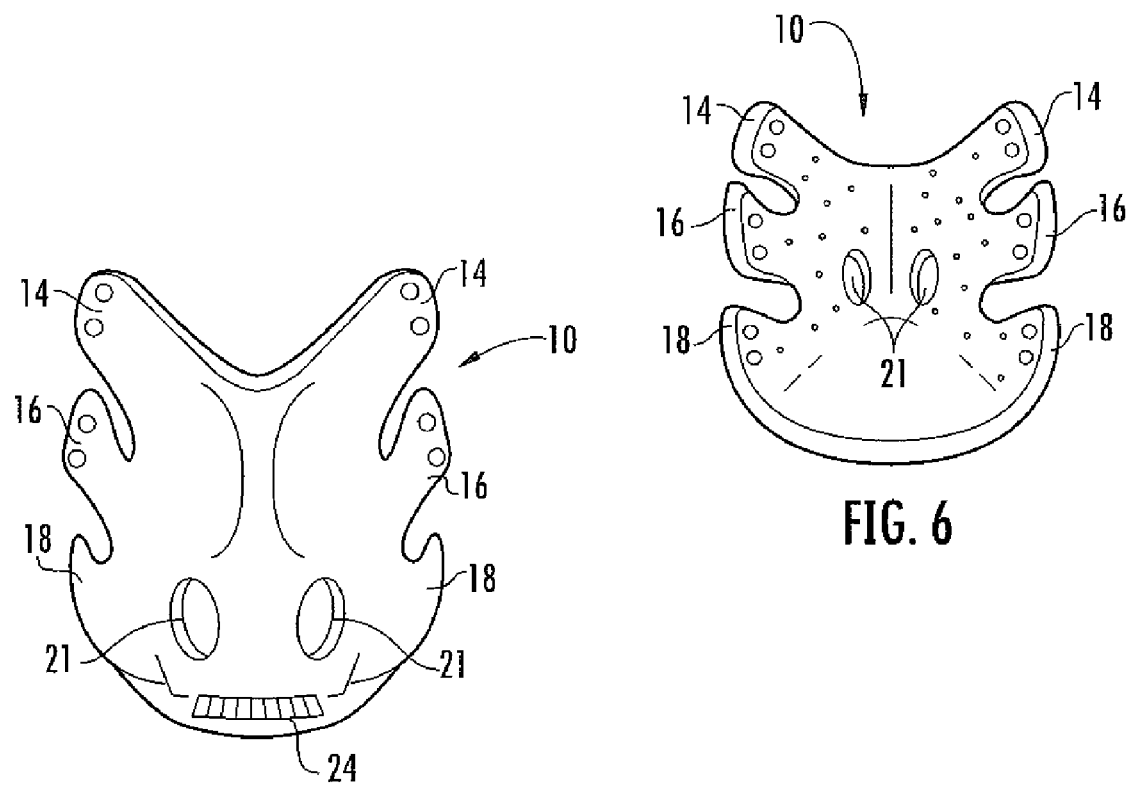
FIG. 5
FIG. 6

US 7,850,631 B2

FOOT ABDUCTION BRACING APPARATUS

BACKGROUND OF THE INVENTION

Dr. Ignacio Ponseti is an internationally famous physician and surgeon specializing in the treatment and management of a childhood deformity commonly know as a club foot. Dr. Ponseti has for many decades promoted the use of a foot and ankle abduction device, or orthosis, that is used to correct and prevent relapses of the club foot deformity. These abduction devices typically consist of a rigid bar connected between shoes worn by the child which bar separates the feet of the child and holds the feet in an outward rotation or abduction. Typically, if the condition is diagnosed early enough, this device is worn full-time for a period of months, but during the period of treatment, the angle of outward rotation is periodically adjusted.

The Ponseti technique, as it has become known throughout the world, has been highly successful in treating club feet without the necessity of corrective surgery. Many devices have been designed and used for many years in applying the Ponseti technique. Currently used devices that apply the Ponseti technique are shown in U.S. Pat. No. 7,267,657. In this patent, there are disclosed improvements in such devices which provide for quick release of the shoes from the abduction bar and which also provide a method for varying the abduction angle and locking it in place at a selected angle. Devices of this type have been extremely successful and are widely used by those who treat patients using the Ponseti technique. However, the devices are relatively expensive, and in many countries throughout the world, the cost prohibits widespread usage. There is therefore a need for an improved but yet relatively inexpensive orthosis for use in treating club feet using the Ponseti technique.

SUMMARY OF THE INVENTION

The improved foot abduction brace device of the invention is a relatively simple device in which the shoe and abduction bar are connected by a simple fastening device such as a set screw, and in which the abduction bar is a single bar that can be bent by the treating physician to hold the shoes in the desired degrees of abduction and dorsiflexion. The abduction bar is bent near the heel portion of the shoe and is made of a material that allows the bar to retain the selected position once bent. However, the bar must be sufficiently strong so that the child cannot bend the bar and therefore change the abduction angle.

BRIEF DESCRIPTION OF THE DRAWING

FIG. 4 is a perspective view generally from the bottom of the shoe and showing one embodiment of the shoe that is adapted to be attached to the bar of FIG. 3;

FIG. 5 is a rear view of the shoe of FIG. 4;

FIG. 6 is a front view of the shoe of FIG. 4;

DESCRIPTION OF THE PREFERRED EMBODIMENTS OF THE INVENTION

Figure 1:
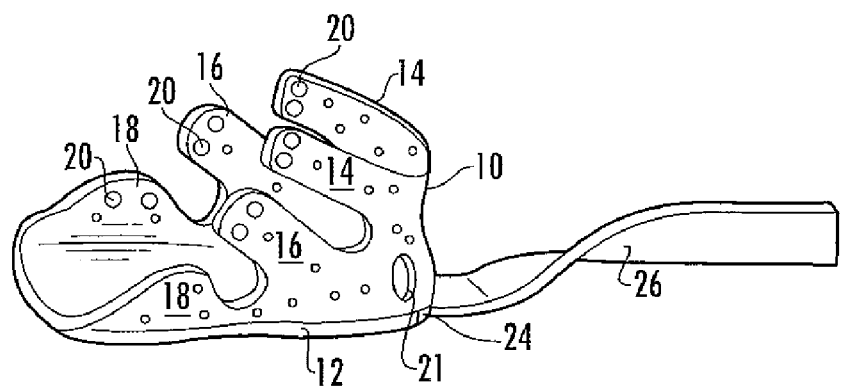
FIG. 1 is a perspective view generally from the side of the shoe and showing the one-piece shoe and bar connected.

Referring first to FIG. 1, there is illustrated a device constructed according to the principles of the invention and employing a shoe 10 that incorporates in the shoe a separate foot plate 12 to form a one-piece device. The shoe 10, sometimes referred to as a "gauntlet," is preferably made of a polyurethane-based compound or a polymer, a thermal molded material, or rubber—all of which are strong elastic synthetic substances. The shoe 10 includes an upper strap 14, a middle strap 16, and a lower strap 18 on each side of the shoe 10. The straps on each side of the shoe 10 are connected across the foot and ankle of the patient in any suitable manner such as by laces (not shown) that extend through the openings 20 in the straps 14, 16 and 18. A hole 21 is preferably formed on each side of the shoe 10 near the heel portion so as to check to make certain the heel of the patient is in the correct place down and back. In the embodiment of FIG. 1, the foot plate 12 is molded into the shoe 10 in any suitable manner to form the single structure. The foot plate 12 is formed of a material that provides rigidity to the device, and is formed preferably of urethane or thermal molded plastic. The foot plate 12 includes a slot 24 for receiving one end of the abduction bar 26. Once the abduction bar 26 is inserted into the slot 24, it is held in place by a suitable fastening member such as set screw 28 threaded into an opening 30 formed in the side of the foot plate 12. Although not shown in the drawings, it will be obvious to those skilled in the art that the other end of the abduction bar 26 is inserted into the other of the pair of shoes 10. The abduction bar 26 is preferably formed from an aluminum alloy or other suitable metal or composite material that has the properties which allow it to be bent into selected positions and retain in its memory the degree to which the bar is bent. The material of the abduction bar 26 must also have sufficient strength so that the child cannot bend the bar once it has bent into the desired abduction position by the therapist or physician. The abduction bar 26 is constructed so that it can hold the pair of shoes 10 in the desired degree of abduction, usually between 60° and 70° and 10-15° of dorsiflexion. The material of the abduction bar 26 allows the position of both shoes to be changed to more or less abduction or more or less dorsiflexion by bending the bar near the heel portion of the shoe 10. This allows the abduction bar 26 to be bent to various positions to change the abduction or dorsiflexion throughout the period of treatment of the patient. This is done in a very simple manner and thus greatly reduces the cost of this type of appliance used in the application of the Ponseti method.

Figure 2:
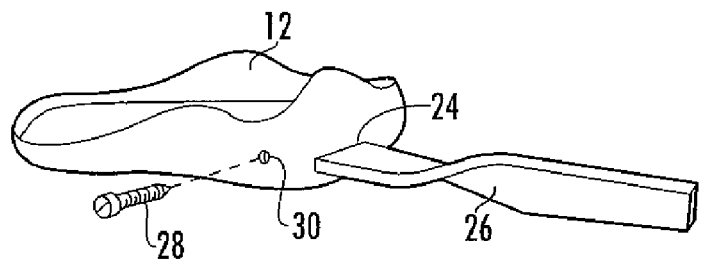
FIG. 2 is a perspective view from a slightly different angle than that of FIG. 1 and showing the one-piece molded foot plate and bar connected.
Figure 3:
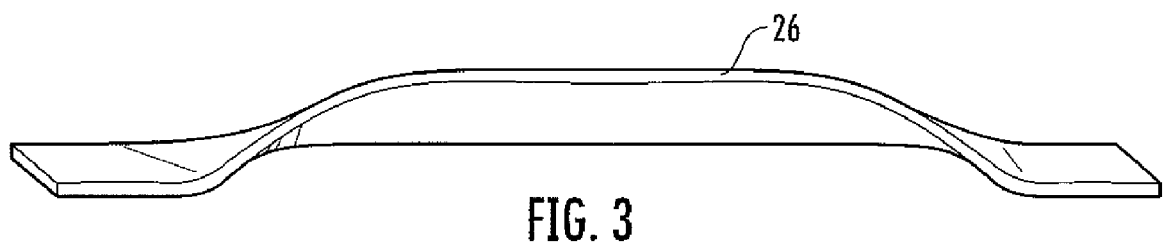
FIG. 3 is a perspective view showing the abduction bar in a selected position.

Referring now to FIGS. 4, 5 and 6, there is shown another embodiment of the foot abduction brace device with FIGS. 4, 5 and 6 showing the shoe 10 as a separate component from the foot plate 12. In other words, the shoe shown in FIGS. 4, 5 and 6 is attached in any suitable manner to inside surface of the foot plate 12 of FIG. 2. Attachment of the shoe 10 to the foot plate 12 can be done in any suitable manner such as by use of a suitable adhesive. This embodiment of FIGS. 4, 5 and 6 may be useful for applications in which the manufacturer of the abduction brace device as a molded one-piece shown in FIG. 1 is not practical or cost effective. In all other respects, the design of the shoe 10 in FIGS. 4, 5 and 6 is identical to that described with reference to the one-piece structure of FIG. 1.

Figure 7:
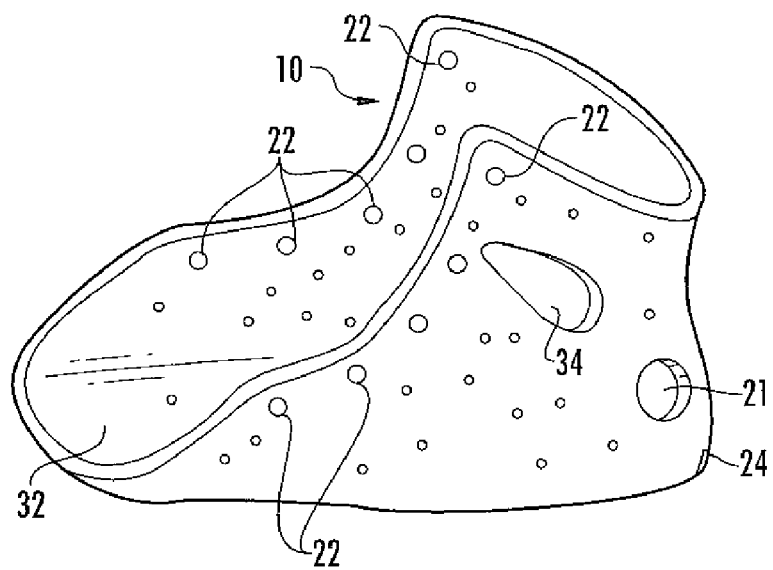
FIG. 7 is a perspective view generally from the side showing another embodiment of the shoe.
Figure 8:
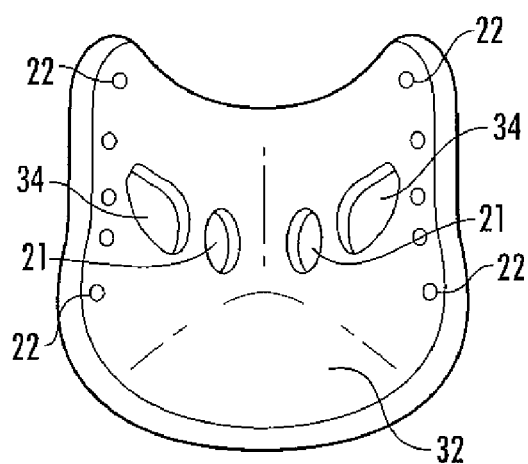
FIG. 8 is a front view of the shoe of FIG. 7.
Figure 9:
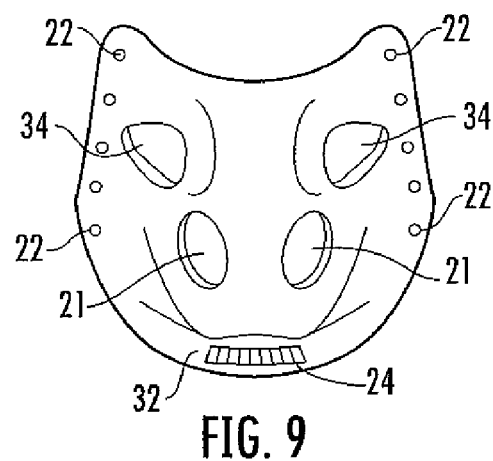
FIG. 9 is a rear view of the shoe of FIG. 7.

Referring now to FIGS. 7, 8 and 9, there is shown another embodiment of the shoe portion of the foot abduction brace device of the invention. In this embodiment, the shoe 10 and foot plate (not shown separately in this embodiment) are formed in a single molded process in which the sole portion 32 is molded to be sufficiently stiff to receive the abduction bar 26. Also, the embodiment of the shoe 10 in FIGS. 7, 8 and 9 does not have separate straps but rather a continuous upper portion containing holes 22 to receive suitable laces or other fastening means. This embodiment of FIGS. 7, 8 and 9 also contains an additional hole 34 which relieves pressure and therefore minimizes the possibility of blisters forming on the patient's foot and ankle at this pressure point. In all other respects, the shoe shown in this embodiment functions in the same manner as the other embodiments of the invention.

Having described various embodiments of the invention, it will be obvious to those skilled in the art that the foot abduction brace device of this invention is a very simple and therefore less costly version of an abduction brace device that can be used in applying the Ponseti method. The device of the invention therefore will have application for use in areas, such as third world countries, where the need is great but funds are not available to supply the more sophisticated designs of this type of device.

Having thus described the invention in connection with the preferred embodiments thereof, it will be evident to those skilled in the art that various revisions can be made to the preferred embodiments described herein with out departing from the spirit and scope of the invention. It is my intention, however, that all such revisions and modifications that are evident to those skilled in the art will be included with in the scope of the following claims.

What is claimed is as follows:

1. A foot abduction apparatus for maintaining a patient's feet in a predetermined therapeutic arrangement, the apparatus comprising:
   a rigid elongated abduction member having a left end and a right end;
   a right shoe operatively combined with the right end of the elongated abduction member;
   a left shoe operatively combined with the left end of the elongated abduction member;
   the right and left shoes each comprised of an upper portion for securing the shoe to the patient's foot and ankle;
   a foot plate for each shoe;
   the foot plate molded into the shoe to form a single structure;
   each foot plate having a slot formed therein to directly receive an end of the elongated abduction member;
   a fastener combined with each foot plate and an end of the elongated abduction member to removably secure the elongated abduction member to the foot plate; and
   the shoes being made of a strong elastic material to secure them to the feet of the patient and the elongated abduction member being made of a suitable material that allows the elongated abduction member to be bent so as to place the patient's feet at a desired angles of abduction and dorsiflexion, wherein the angles can be periodically adjusted, but the elongated abduction member cannot be bent by the patient.

2. The foot abduction apparatus of claim 1 in which the upper portion of each shoe is provided with a plurality of holes and laces are woven through the holes to secure the shoe to the patient's foot.

3. The foot abduction apparatus of claim 1 in which the foot plate is formed of a material that provides rigidity to the shoe.

4. The foot abduction apparatus of claim 3 in which in which the material of the foot plate is a thermal molded plastic substance.

5. The foot abduction apparatus of claim 4 in which the foot plate and upper portion of each shoe are one piece.

6. The foot abduction apparatus of claim 4 in which the foot plate and upper portion of each shoe are one piece and are formed by a single molded process.

7. The foot abduction apparatus of claim 4 in which the foot plate and shoe are separate components.

8. The foot abduction apparatus of claim 1 in which the upper portion of each shoe is provided with one or more openings to relieve pressure on the patient's foot and ankle.

9. The foot abduction apparatus of claim 1 in which the fastener is a set screw.

10. The foot abduction apparatus of claim 1 wherein: the abduction member is an aluminium alloy.

* * * * *